United States Patent [19]

Baker

[11] Patent Number: 5,104,409
[45] Date of Patent: Apr. 14, 1992

[54] MAMMARY IMPLANT

[76] Inventor: James L. Baker, 1017 Temple Grove, Winter Park, Fla. 32789

[21] Appl. No.: 666,642

[22] Filed: Mar. 8, 1991

Related U.S. Application Data

[62] Division of Ser. No. 295,434, Jan. 10, 1989, Pat. No. 5,026,394.

[51] Int. Cl.⁵ .............................................. A61F 2/12
[52] U.S. Cl. ........................................... 623/8; 623/66
[58] Field of Search ...................... 623/7, 8, 11, 12, 66, 623/901

[56] References Cited

U.S. PATENT DOCUMENTS

| | | | |
|---|---|---|---|
| 4,332,634 | 6/1982 | Aperavich | 623/8 |
| 4,685,447 | 8/1987 | Iversen et al. | 623/8 |
| 4,908,029 | 3/1990 | Bark et al. | 623/8 |
| 4,960,425 | 10/1990 | Yani et al. | 623/8 |

FOREIGN PATENT DOCUMENTS 2040688  9/1980  United Kingdom .................... 623/8

*Primary Examiner*—David Isabella
*Assistant Examiner*—Debra S. Brittingham
*Attorney, Agent, or Firm*—Rodman & Rodman

[57] ABSTRACT

The mammary implant includes a shell with a base portion and a reinforcement member provided at the base portion. The shell also includes a promontory portion that projects from the base portion. The reinforcement member can be formed with materials of different hardnesses, or of different thicknesses in different areas. The reinforcement member can also be formed with ribs, rings or grooves at various areas of the reinforcement member to enhance flexibility or rigidity. The reinforced mammary implant prevents casular contracture due to scar tissue formation after implantation and thus maintains a desired profile and softness of the implanted prosthesis.

11 Claims, 3 Drawing Sheets

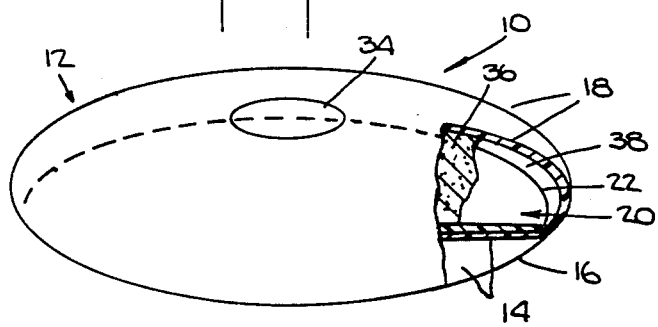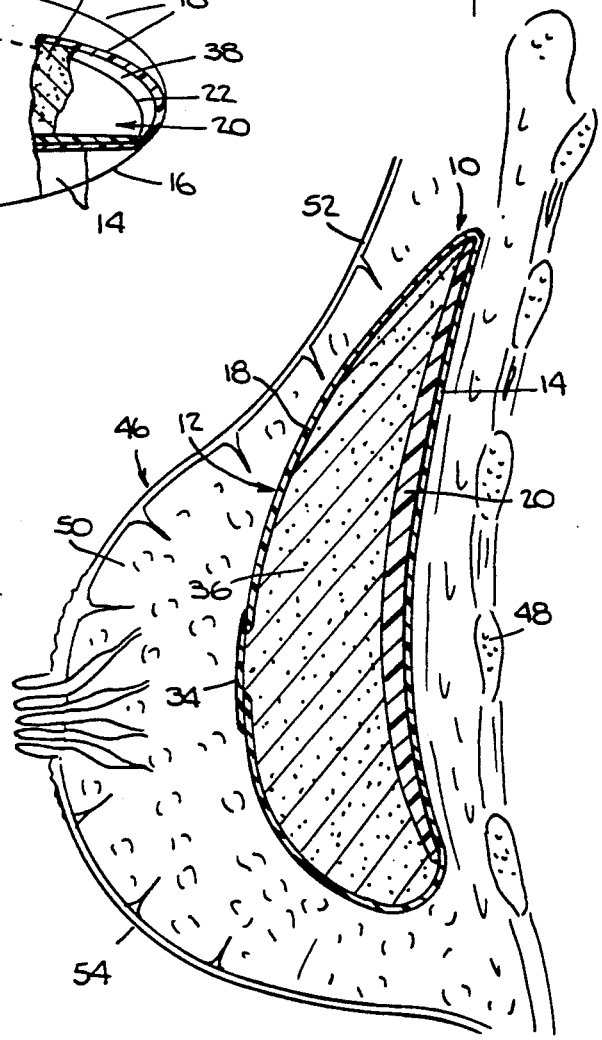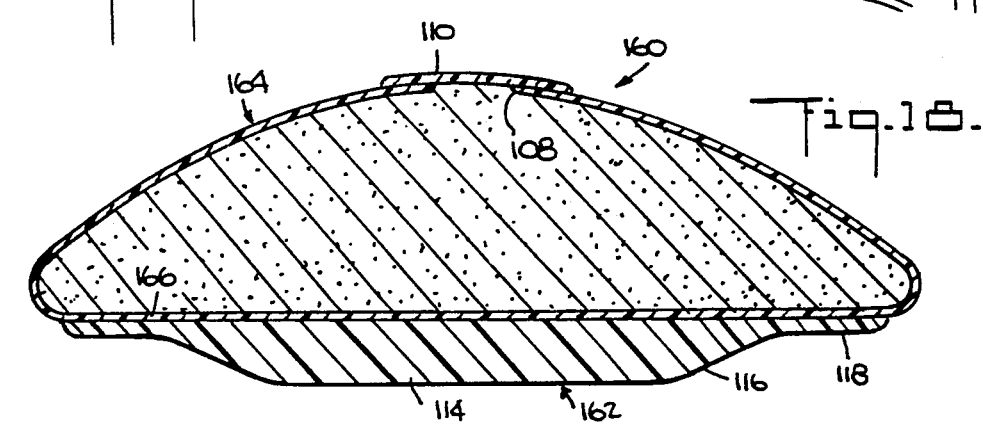

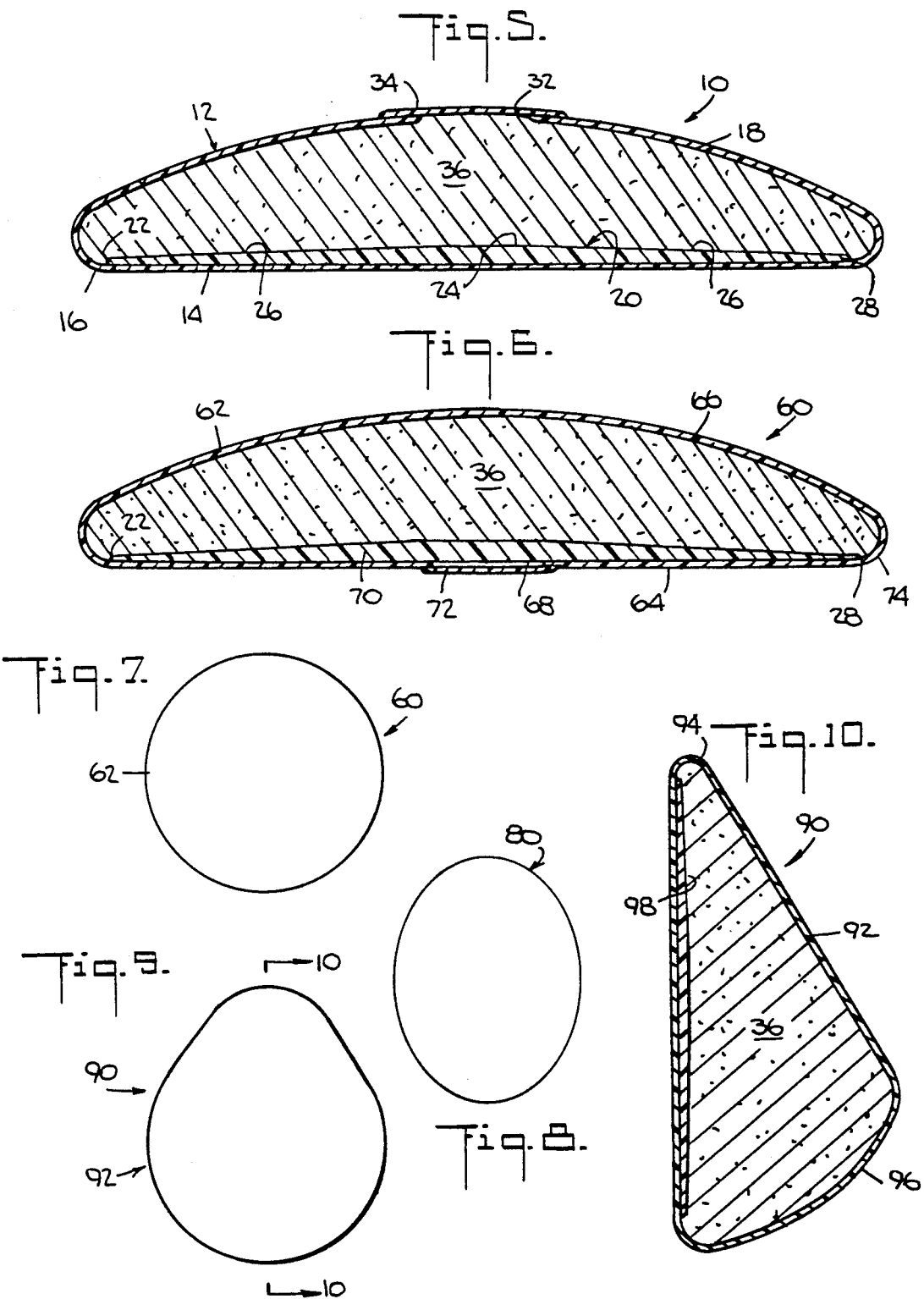

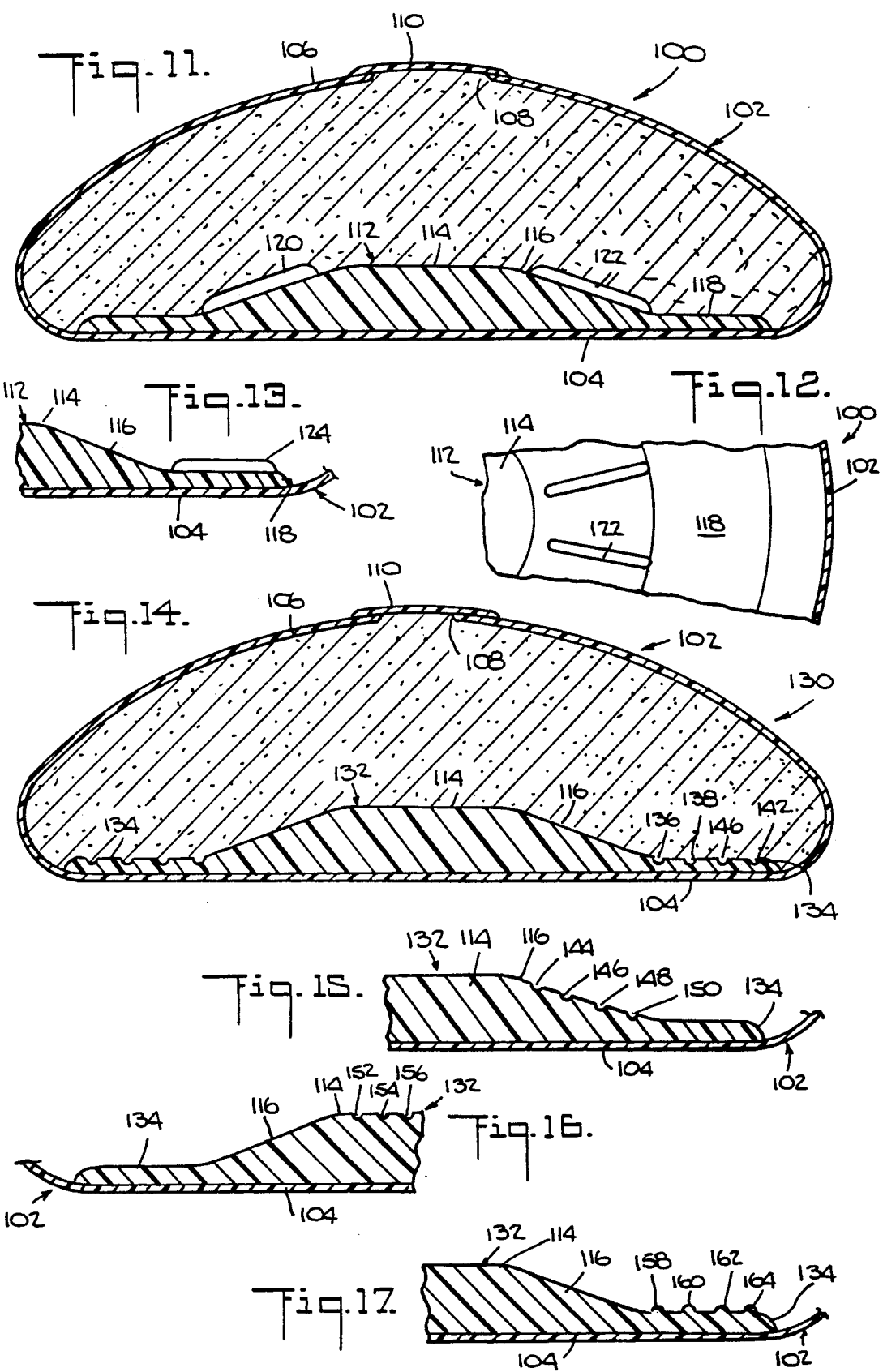

MAMMARY IMPLANT

This is a division of application Ser. No. 295,434, filed Jan. 10, 1989 U.S. Pat. No. 5,026,394.

BACKGROUND OF THE INVENTION

This invention relates to mammary prostheses and more particularly to a novel contracture resistant breast implant.

Breast implants or prostheses used for breast augmentation and for breast reconstruction generally include a soft, flexible plastic envelope containing a cohesive gelatinous material. The envelope can for example, be of a semi-spherical, semi-teardrop or semi-oval shape. Other selected shapes can also be used depending upon the particular needs of a patient. Generally, the envelope is not filled to capacity and the quantity of gel provided enables the contour or shape of the envelope to be easily indented, deformed or compressed.

A common technique for implanting the prosthesis is to make an incision at the base of the breast on the infra-mammary fold under the curve of the breast. A pocket, either directly below the breast or below the pectoralis muscle is made by working through the incision. The pocket can be formed behind the breast tissue or underneath the muscle. The prosthesis is thus placed in this pocket and the incision is closed.

Following implantation, healing scar tissue forms around the implant substantially encapsulating the implant. This scar tissue capsule frequently contracts the pocket in which the implant is disposed. Such contracture exerts external pressure on the implant that deforms the semi-spherical, semi-teardrop or oval shape of the prosthesis. In extreme cases of scar tissue contracture, the scar tissue capsule will cause the prosthesis to contract to a geometric configuration which holds the most volume in the least available space, such as a spherical shape. This condition is known as "spherical contracture".

Scar tissue contracture causes the gel within the implant to become pressurized thereby forming a local rigidification under the breast, with a resulting firmness that is undesirable and often painful. In addition, the initial shape of the augmented or reconstructed breast may become more spherical because of the capsular induced contraction of the implant. The change in shape of the breast to an undesirable spherical form is the most common complication of breast implant surgery, occurring in up to 65% of cases reported in recent studies.

U.S. Pat. No. 4,264,990 to Hamas, for a mammary prosthesis attempts to deal with the phenomena of capsular contractures of an implant by providing the implant with a backing having spaces into which a curable rigidifying material is provided. The curing and rigidification takes place after implantation and the rigidified backing is intended to prevent scar tissue contracture of the prosthesis to obviate hardening of the implant. The Hamas device thus requires a special treatment process of the prosthesis prior to implantation. The treatment process requires skill and the need for additional preparation time of the prosthesis. The disclosed use of a material which is intended to cure within a patient to provide a desirable rigidity is accompanied by a risk that such material may not cure properly, or through inadvertence, may leak or otherwise become unconfined from the implant causing adverse affects to the patient.

U.S. Pat. No. 4,298,997 to Rybka, also deals with the problems of fibrous capsular contractures in silicone breast implants. Rybka suggests that a spacer device in the form of a thin silicone sheet be adhered to the implant to provide a base for the implant. An annular strip of Dacron felt is secured to the periphery of the disk to permit ingrowth of tissue and provide an anchor for the scar tissue capsule. The silicone sheet and annular Dacron band do not function as a reinforcement for preventing contracture of an implant. The Rybka device thus relies on a controlled growth of scar tissue to form an anchor for an implant in order to limit the constricting affect of such scar tissue. However, the presence of Dacron, even in small amounts, has been shown to cause excessive scar tissue formation in the entire capsule surrounding the implant, thus frequently producing an undesirable degree of spherical contracture.

It is thus desirable to provide a mammary prosthesis which does not allow scar tissue contracture to occur, does not require special structural preparation before implantation, and does not rely on a particular direction of scar tissue growth to limit the constricting effect of such scar tissue.

OBJECTS AND SUMMARY OF THE INVENTION

Among the several objects of the invention may be noted the provision of a novel breast implant that prevents scar tissue contractures from occurring, a novel reinforced breast implant, a novel breast implant that has a reinforcement member that is substantially firmer than the gelatinous filler material, a novel breast implant with a reinforcement member that achieves selected levels of firmness by varying durometers of reinforcement material, varying member thickness and/or providing inclusions of ribs, rings or grooves at various areas of the reinforcement member, a novel breast implant that includes a self-contained reinforcement member, a novel breast implant which has a reinforcement member formed as an integral part of the shell or as a separate component mechanically bonded to the shell, a novel breast implant that is formed entirely of bio-compatible materials and a novel method of making a mammary implant.

Other objects and features of the invention will be in part apparent and in part pointed out hereinafter.

In accordance with the present invention, the mammary implant includes a soft, flexible, hollow shell having a shell base and a collapsible promontory portion. A cohesive filler material of predetermined volume is provided in the shell to prevent collapse of the promontory portion and to permit the promontory portion to project or drape in a predetermined manner from the shell base.

The implant includes a resilient, nondeformable, substantially rigid reinforcement member joined to the shell base or formed as an integral part of the shell. The reinforcement member has a periphery that substantially corresponds in size and shape to that of the shell base but may be of slightly lesser or greater magnitude than the shell base. The reinforcement member can also be joined to the shell base so as to determine the maximum peripheral base magnitude of the implant.

The shell is preferably a molded structure and the molding process results in the formation of an opening in the shell where a rod joins the mandrel or mold form.

The shell opening facilitates installation of the reinforcement member by, for example, bonding the reinforcement member to the interior base portion of the shell and then turning the shell inside out. Alternatively the shell can be stretched around the area of the opening to permit insertion of the reinforcement member. The reinforcement member is thus bonded to the base portion of the shell after it has been inserted within the shell.

In one embodiment of the mammary implant the shell has a generally spherical shape in plan view. Other embodiments include a oval shape and a teardrop shape. In each embodiment, selected levels of firmness of the reinforcement member may be achieved by varying the durometer of the reinforcement material, varying the reinforcement member thickness and/or providing inclusions of ribs, rings or grooves at various areas of the reinforcement member.

The reinforcement member prevents the scar tissue capsule from forming a spherically-shaped pocket, by keeping the pocket open at the base. If the scar tissue capsule cannot grow into a sphere, it cannot place uniform compression on the implant. Thus the prosthesis is essentially contracture resistant and maintains its desired profile and natural shape.

In other embodiments of the invention the opening in the shell can be provided at the base portion.

The invention accordingly comprises the constructions and method hereinafter described, the scope of the invention being indicated in the claims.

DESCRIPTION OF THE DRAWINGS

In the accompanying drawings,

FIG. 1 is a simplified perspective view of a mammary prosthesis incorporating one embodiment of the invention;

FIG. 2 is a simplified exploded view of two components thereof prior to assembly;

FIG. 3 is a fragmentary sectional view of the base portion thereof;

FIG. 4 is a full sectional view thereof in implanted position;

FIG. 5 is a full sectional view thereof prior to implantation;

FIG. 6 is a sectional view of another embodiment thereof;

FIG. 7 is a simplified plan view thereof;

FIGS. 8 and 9 are simplified plan views of further embodiments thereof;

FIG. 10 is a sectional view taken along the line 10—10 of FIG. 9;

FIGS. 11 and 13–18 are sectional views of further embodiments of the invention; and, FIG. 12 is a fragmentary plan view of FIG. 11.

Corresponding reference characters indicate corresponding parts throughout the several views of the drawings.

DETAILED DESCRIPTION OF THE INVENTION

A mammary implant incorporating one embodiment of the invention is generally indicated by the reference number 10 in FIG. 1.

The mammary implant 10 includes a soft, flexible, hollow shell 12, preferably formed of silicone. The shell 12, which can be molded on a mandrel (not shown) of complementary shape, has a base portion 14 with a generally circular periphery 16. The shell 12 also has a promontory portion 18 with a dome-like contour, occasionally referred to as semi-spherical, but more like a flattened hemisphere.

The shell 12 is reinforced at the base 14 by a reinforcement member 20, preferably formed of silicone and having a periphery 22 that substantially corresponds in shape to the circular periphery 16 of the base portion 14. As most clearly shown in FIG. 5, the reinforcement member 20 has a central portion 24 of uniform thickness and a portion 26 of nonuniform thickness that tapers from the central portion 24 toward the peripheral edge 22, which is rounded as noted at 28. The peripheral extent of the reinforcement member 20 is of lesser magnitude than the periphery 16 of the base portion 14.

A predetermined medial section of the reinforcement member 20, such as the central portion 24, can be formed of silicone characterized by a hardness of 70–90 Durometer, for example. A predetermined annular section of the reinforcement member 20, such as the tapered section 26, can be made of silicone characterized by a hardness reading of 20–30 Durometer, for example.

The reinforcement member 20 is adhered to the base portion 14 of the shell 12 by raw silicone or silicone adhesive as indicated by the reference number 30 in FIG. 4. A silicone patch 34 which can be of the same gauge as the shell 12 is placed across the opening 32 and adhered with raw silicone or silicone adhesive.

A gelatinous material 36 such as a silicone gel is provided in a space 38 between the promontory portion 18 and the reinforcement member 20 in any suitable known manner. The amount of gelatinous material 36 provided in the space 38 enables the promontory portion 18 of the shell 12 to be easily indented or compressed.

The mammary prosthesis 10 is thus a sealed unit with a self-contained reinforcement member 20 and can be used without any further structural embellishments.

Implantation of the mammary prosthesis 10 in a breast 46 is schematically shown in FIG. 4 wherein the prosthesis 10 is positioned anteriorly of the rib cage or chest wall 48. The mammary implant is designed to have substantially the same consistency as that of the natural breast tissue 50. The ability of the gel within the implant to drape or shift in response to changes in position, results in a narrowing of the implant 10 near an upper portion 52 of the breast 46 and an enlarging of the implant 10 at a lower portion 50 of the breast 46. The draping effect of the implant 10 corresponds to the natural shape of the breast.

When scar tissue forms around the implant 10, capsular contraction will tend to form the pocket containing the implant into a spherical shape. External forces exerted on a prosthesis due to such capsular contraction ordinarily deform the prosthesis into a spherical shape and curtail the ability of the implant to drape or shift in response to changes in position. However the reinforcement member 20 within the shell 12 prevents scar tissue contractures from occurring and thus maintains the intended profile of the prosthesis 10.

The formation of the reinforcement member 20 with two different grades of silicone for example, helps facilitate implantation of the prosthesis 10 by enabling the prosthesis to be slightly bent, folded or otherwise reduced in size. Thus the prosthesis can be passed through an infra-mammary incision (not shown) that is smaller than an incision needed for an implant of comparable size that cannot be bent, folded or otherwise reduced in size.

Another embodiment of the mammary implant is generally indicated by the reference number 60 in FIG. 6. The mammary implant 60 includes a shell 62 having a generally circular base portion 64 and a promontory portion 66. However, an opening 68 corresponding to the opening 32 of the implant 10 is formed at the base portion 64. A reinforcement member 70 identical to the reinforcement member 20 is secured to the base portion 64 over the opening 68. A patch 72 identical to the patch 34 is used to close the opening 68. The implant 60 is otherwise similar to the implant 10.

Another embodiment of a mammary implant is generally indicated by the reference number 80 in FIG. 8. The implant 80 has an oval periphery, which may be more desirable than the circular periphery for some patients. The mammary implant 80 is otherwise similar to the implant 10.

Another embodiment of the mammary implant is generally indicated by the reference number 90 in FIG. 9. The mammary implant 90 includes a shell 92 with a teardrop shape. The implant 90 when draped has relatively narrow girth at an end portion 94 and relatively wide girth at an end portion 96 to provide a desired profile. A reinforcement member 98 disposed in the shell 92 has a outer peripheral shape which corresponds to the teardrop shape. The reinforcement member 98 can be a structure similar to that previously described for the reinforcement member 20. However the shape of the central portion (not shown) can be circular or teardrop. The reinforcement member 98 prevents capsular contraction from occurring to maintain the integrity of the desired profile as shown in FIG. 10.

Another embodiment of the mammary implant is generally indicated by the reference number 100 in FIG. 11. The mammary implant 100 includes a shell 102 having a generally circular base portion 104 and a promontory portion 106. The shell 102 includes an opening 108 and a patch 110 identical to the opening 32 and the patch 34 of the implant 10.

A reinforcement member 112 provided at the base portion 104 includes a medial section 114, an annular tapered section 116 and an annular peripheral section 118 of less thickness than the medial section 114. The entire reinforcement member 112 may be of one Shore A Durometer material.

Different levels of flexibility at various areas of the reinforcement member can be accomplished by varying the structural dimensions of the reinforcement in the areas of interest. For example, there is a gradual change of flexibility of the reinforcement member in the annular tapered section 116 because of the gradual change of thickness. The annular peripheral section 118 is the most flexible portion of the reinforcement member 112 because it has the thinnest cross section.

If desired, radially extending ribs such as 120 and 122 can be provided at the tapered section 116 to enhance the rigidity of the reinforcement member 112. Although not shown, the ribs 120 and 122 can also extend continuously into the medial section 114, and/or into the peripheral section 118. Reinforcing ribs can also be localized in other selected areas of the reinforcement member as for example, the rib 124 at the peripheral section 118 of FIG. 13. The implant 100 is otherwise structured and used in a manner similar to the implant 10.

Another embodiment of the mammary implant is generally indicated by the reference number 130 in FIG. 14. The mammary implant 130 differs from the implant 100 in the structure of the reinforcement member 132. The reinforcement member 132 includes a peripheral section 134 with flexibility enhancing annular grooves such as 136, 138 and 140 and 142 for example. Any selected number of flexibility enhancing grooves 142–146 can be provided at any selected areas of the reinforcement member 132 to enhance flexibility, such as the grooves 144, 146, 148 and 150 at the tapered section 116 of FIG. 15 and the grooves 152, 154 and 156 at the medial section 114 of FIG. 16.

If desired, the reinforcement member 112 can be provided with any selected number of reinforcement rings such as 158, 160, 162 and 164 at any selected area of the reinforcement member such as at the peripheral section 134 (FIG. 17) to enhance rigidity. The reinforcement rings 158–164 can be used on the reinforcement member 132 without the flexibility enhancing grooves 136–142. However, reinforcement rings can be used at one section of the reinforcement member 132 and reinforcement grooves can be used at a different section of the same reinforcement member 132. The implant 130 is otherwise similar to the implant 100.

Another embodiment of the mammary implant is generally indicated by the reference number 160 in FIG. 18. The mammary implant 160 differs from the mammary implants 100 and 130 by provision of a reinforcement member 162, similar to the reinforcement members 112 and 132 on the outside of the shell 164. The outside diameter of the reinforcement member 162 can be of a greater or lesser magnitude than the periphery of the base portion 166 of the shell 164. The mammary implant 160 is otherwise similar to the mammary implants 100 and 130.

If desired the reinforcement member and/or the shell in any of the previously described embodiments can incorporate a fabric reinforcement such as Dacron.

Based on the structural variations of the previously described embodiments, it will be noted that the reinforcement member may have any one or more of the following characteristics:

(1) The entire reinforcement member may be of one uniform thickness.
(2) The medial portion of the reinforcement member may be thicker than the peripheral portion thereof.
(3) [The medial portion of the reinforcement member
(4) The medial portion of the reinforcement member may be of a firm Shore A Durometer material with the outer peripheral portion being a softer Shore A Durometer material.
(5) The reinforcement member can be provided with formations that enhance the rigidity or flexibility, such as radially extending ribs to enhance the rigidity, annular rings to enhance the rigidity and annular grooves to enhance the flexibility. The ribs, rings or grooves can be placed at any portion of the reinforcement member in any selected quantity.
(6) The outer magnitude of the reinforcement member may be greater or smaller than the outer peripheral portion of the shell of the mammary implant. The reinforcement member is usually of a larger magnitude than the outer peripheral portion of the shell when the reinforcement member is provided on the outside surface of the shell.
(7) The reinforcement member may be attached to the inside or outside of the shell with raw silicone or silicone adhesive.
(8) The shell component and the reinforcement member can be formed as an integral unit.

Some advantages of the invention evident from the foregoing description include a mammary prosthesis that effectively resists the forces of capsular contracture to maintain a desired implant profile. The prosthesis is entirely self contained and does not require any structural additions by a physician resulting in less handling of the implant by a physician. All components of the implant are biocompatible. A further advantage is that the implant does not become rigid and does not deleteriously affect the consistency of the natural breast tissue. The natural qualities of the breast are thus maintained.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A method of making a mammary prosthesis comprising
   a. forming a hollow, collapsible shell from a flexible, stretchable material and providing an opening of predetermined size in the wall of the shell,
   b. inserting a resilient, nondeformable, substantially non-compressible reinforcement member of greater size than the opening of the shell into the shell,
   c. joining the shell to the reinforcement member,
   d. supplying a predetermined amount of cohesive filler material in the shell to project a portion of the shell from the reinforcement member, and
   e. sealing the opening in the shell to confine the filler material therein.

2. The method of claim 1 wherein the step of sealing includes placement of a patch of shell material across the opening.

3. The method of claim 1 wherein the step of sealing includes placement of the reinforcement member across the area of the opening.

4. The method of claim 1 wherein the step of inserting includes stretching the shell in the area of the opening to permit accommodation of the reinforcement member in the shell.

5. A method of making a mammary prosthesis comprising
   a. forming a hollow, collapsible shell from a flexible, stretchable material and providing an opening of predetermined size in the wall of the shell,
   b. inserting a resilient, nondeformable, substantially non-compressible reinforcement member of greater size than the opening of the shell into the shell,
   c. joining the shell to the reinforcement member,
   d. supplying a predetermined amount of cohesive filler material in the shell to project a portion of the shell from the reinforcement member,
   e. sealing the opening in the shell to confine the filler material therein, and wherein the step of inserting includes turning the shell inside out, and after the joining step, turning the shell outside in.

6. A method of making a mammary prosthesis comprising
   a. forming a hollow, collapsible shell from a flexible, stretchable material and providing an opening of predetermined size in the wall of the shell,
   b. forming a reinforcement member of resilient, nondeformable, substantially non-compressible material with a median portion that has a first level of flexibility and a peripheral portion that has a second level of flexibility greater than the first level of flexibility, and of greater size than the opening of the shell,
   c. inserting the reinforcement member into the shell,
   d. joining the shell to the reinforcement member,
   e. supplying a predetermined amount of cohesive filler material in the shell to project a portion of the shell from the reinforcement member, and
   f. sealing the opening in the shell to confine the filler material therein.

7. The method of claim 6 including forming the median portion of the reinforcement member to a first predetermined thickness and the peripheral portion to a second predetermined thickness that is less than the first predetermined thickness such that the peripheral portion is more flexible than the median portion.

8. The method of claim 6 including providing the reinforcement member with a predetermined minimum stiffness to enable the prosthesis to resist scar tissue contractures.

9. The method of claim 6 wherein the first and second levels of flexibility are obtained by forming the median portion with one predetermined harness and the peripheral portion with a second predetermined harness.

10. The method of claim 6 wherein the first and second levels of flexibility are obtained by forming at least one recess in the peripheral portion.

11. The method of claim 6 wherein the first and second levels of flexibility are obtained by forming the peripheral portion such that is tapers from the median portion.

* * * * *